United States Patent [19]

Suzuki et al.

[11] Patent Number: 4,524,213

[45] Date of Patent: Jun. 18, 1985

[54] DICYCLOPENTADIENE DICARBOXYLIC ACID DERIVATIVES AND PROCESS FOR THEIR PREPARATION

[75] Inventors: Hideo Suzuki; Kanji Ohtsuka; Masami Adachi, all of Funabashi, Japan

[73] Assignee: Nissan Chemical Industries Ltd., Tokyo, Japan

[21] Appl. No.: 578,103

[22] Filed: Feb. 8, 1984

[30] Foreign Application Priority Data

Nov. 9, 1983 [JP] Japan .................. 58-210601
Nov. 9, 1983 [JP] Japan .................. 58-210602
Nov. 9, 1983 [JP] Japan .................. 58-210603

[51] Int. Cl.³ .................. C07C 61/29; C07D 307/93
[52] U.S. Cl. .................. 549/235; 560/116; 562/498; 71/88; 71/106; 71/113
[58] Field of Search .................. 549/235; 560/116; 562/498

[56] References Cited

PUBLICATIONS

Journal of the American Chemical Society 98:7 (Mar. 31, 1976) "The Palladium(II) Catalyzed Olefin Carbonylation Reaction, Mechanisms and Synthetic Utility", D. E. James and J. K. Stille, pp. 1810–1823.

*Primary Examiner*—Richard L. Raymond
*Attorney, Agent, or Firm*—Oblon, Fisher, Spivak, McClelland & Maier

[57] ABSTRACT

A compound represented by the general formula:

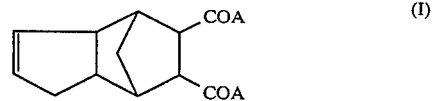

where each A is —OH or —OR where R is an alkyl group, an alkenyl group or a cycloalkyl group, or both A together represent a >O group.

4 Claims, No Drawings

DICYCLOPENTADIENE DICARBOXYLIC ACID DERIVATIVES AND PROCESS FOR THEIR PREPARATION

The present invention relates to novel dicyclopentadiene dicarboxylic acid derivatives and processes for the preparation thereof.

The novel compounds of the present invention are represented by the general formula:

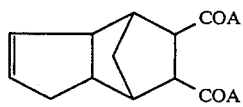

where each A is —OH or —OR where R is an alkyl group, an alkenyl group or a cycloalkyl group, or both A together represent a >O group. When A is —OR, R is preferably a $C_1$–$C_{12}$ alkyl group, a $C_2$–$C_5$ alkenyl group or a $C_5$–$C_6$ cycloalkyl group. Namely, the novel compounds include (a) tricyclo[5,2,1,0$^{2,6}$]dec-3-ene-8,9-dicarboxylic acid anhydride (hereinafter referred to simply as "TCDA") represented by the formula:

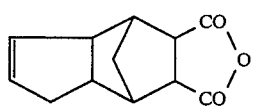

(b) tricyclo[5,2,1,0$^{2,6}$]dec-3-ene-8,9-dicarboxylic acid (hereinafter referred to simply as "TCDC") represented by the formula:

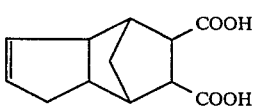

and (c) a tricyclo[5,2,1,0$^{2,6}$]dec-3-ene-8,9-dicarboxylic acid diester (hereinafter referred to simply as "TCDE") represented by the formula

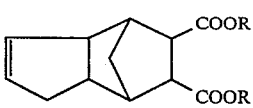

where R is as defined above.

In general, dicarboxylic acid derivatives of this type have a wide range of applications in the field of resins represented by e.g. epoxy thermosetting agents, polyester resins or addition type polyimides, in the field of agricultural medicines such as antimicrobial agents or herbicides and in the field of pharmaceuticals such as precursors for medicines such as CNS (central nerve system) agents or cardiovascular agents. Particularly, in the field of resins, these novel compounds are expected to be useful as starting materials or intermediates for paints, adhesives or polyvinyl chloride plasticizers having superior heat resistance and electric characteristics. With respect to an application of the compounds for the preparation of polyimide derivatives, the present inventors have filed a patent application (i.e. Japanese Patent Application No. 114934/1983).

The compounds of the present invention are prepared by the following reaction steps.

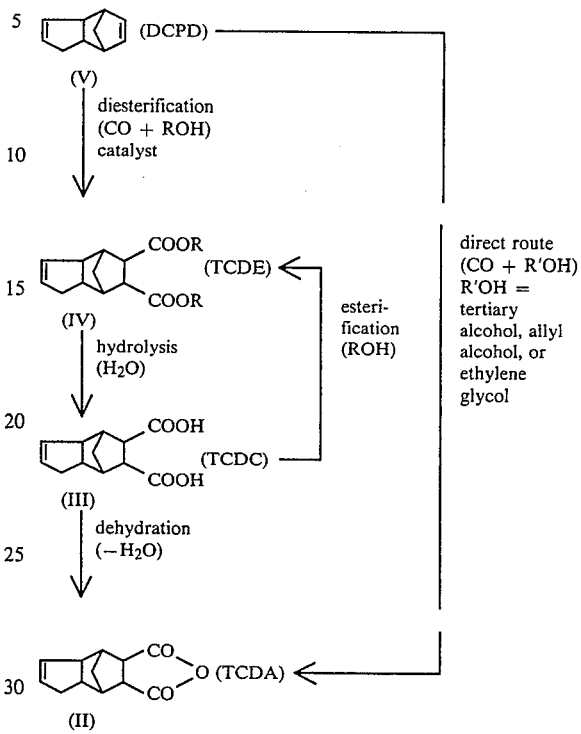

There have been few reports on the direct diesterification of a cycloolefin, except for a study on a cyclomonoolefin reported by J. K. Stille et al. in J. Am. Chem. Soc., Vol. 98, No. 7, p. 1810 (1976).

The present inventors have conducted extensive researches on a method for selectively directly diesterifying one of the double bonds in dicyclopentadiene (hereinafter referred to simply as "DCPD") as a cyclodiolefin, and surprisingly found that the double bond in the norbornene ring can selectively be diesterified without affecting the double bond in the cyclopentene ring, to obtain TCDE in good yield; the ester groups of TCDE can then readily be hydrolyzed to obtain TCDC, which in turn can be dehydrated to obtain TCDA. Further, it has also surprisingly be found that TCDA can be synthesized in a single step directly from DCPD by conducting the diesterification reaction by employing certain specific alcohols. Furthermore, it has been found that TCDE can readily be prepared by the esterification or ester exchange reaction with an optional alcohol. The present invention has been accomplished based on these discoveries.

Thus, the present invention provides the novel compounds represented by the general formula I given above and the processes of their preparation as illustrated by the reaction steps given above.

DCPD of the formula V to be used as the starting material in the present invention is contained in a substantial amount in the $C_5$ fraction obtainable by the cracking of naphtha, and is presently abundantly or excessively available. Accordingly, the industrial significance in the utilization of such material is extremely great.

Now, the present invention will be described in detail with reference to the preferred embodiments.

Initially, the diesterification of the present invention was found to take place by an oxidative addition reaction by means of $Pd^{2+}$. Accordingly, palladium is normally used as the catalyst. However, it has been found that the diesterification reaction proceeds even in the absence of palladium.

Palladium may be employed in various forms, for instance, in the form of an inorganic acid salt, an organic acid salt, a supported palladium or a colloidal metal. Specifically, there may be mentioned palladium chloride, palladium nitrate, palladium sulfate, palladium acetate, palladium propionate, palladium-carbon, palladium-silica, palladium-alumina, palladium-barium carbonate, palladium black and colloidal palladium.

Palladium is used in an amount of at least 0.1 molar % relative to the starting material DCPD, whereby TCDE is obtainable in good yield.

In this reaction, $Pd^{2+}$ is reduced to $Pd°$ by the reaction. Therefore, it is necessary to use an oxidizing agent capable of reconverting $Pd°$ to $Pd^{2+}$. As such an oxidizing agent, it is preferred to use a metal compound having a small redox potential, such an copper or an iron compound. Specifically, cupric chloride, cupric nitrate, cupric sulfate, cupric formate, cupric acetate, ferric chloride, ferric nitrate, ferric sulfate, ferric formate or ferric acetate may be employed. The copper compounds give particularly good results.

These compounds are preferably in the form of anhydrides, whereby TCDE is obtainable in good yield. When they are in the form of hydrates, the yield tends to decrease.

Such an oxidizing agent is required to be used in a stoichiometric amount relative to the starting material. In the diesterification reaction of the present invention, the oxidizing agent is used in an amount of at least 2 mols relative to the starting material DCPD when the palladium catalyst is used in a catalytically effective amount.

On the other hand, as the oxidizing agent, molecular oxygen may be employed without using the metal compounds. It is also possible to use molecular oxygen in combination with the metal compounds.

When molecular oxygen is used as the oxidizing agent, it is desirable to add a dehydrating agent such as methyl orthoformate, methyl orthoacetate, ethyl orthoformate or 1,1-dimethoxycyclohexane, which is a derivative of the alcohol, whereby the yield is remarkably improved.

In the present invention, it has been unexpectedly found that the oxidative addition reaction takes place and the diesterification reaction proceeds even when only the metal compound as the oxidizing agent is used without employing the palladium catalyst. Under this condition, the reaction rate is lower than the case where the metal compound is used in combination with the palladium catalyst, but the selectivity to the desired TCDE is high.

The alcohol to be used as the other starting material for the diesterification, is an alkyl alcohol, an alkenyl alcohol, a cycloalkyl alcohol, a benzene-substituted alkyl alcohol or a benzene-substituted alkenyl alcohol, in which the alkyl or alkenyl group may contain an oxygen or nitrogen atom. The alcohol may be monohydric or polyhydric. Specifically, there may be mentioned methanol, ethanol, butanol, nonanol, tridecanol, cyclohexanol, benzyl alcohol, allyl alcohol, cinnamyl alcohol, furfuryl alcohol, propargyl alcohol, geraniol, nerol, ethylene glycol, propanediol, glycerin, ethanolamine and propanolamine.

Further, the alcohol may be used in the form of its derivative such as an acetal, a ketal or an alkyl orthoformate, whereby the reaction likewise proceeds satisfactorily. For instance, when methyl orthoformate, methyl orthoacetate or 1,1-dimethoxycyclohexane is used, the dimethylester is obtainable in the same manner as in the case where methanol is used.

As the solvent, a hydrocarbon such as pentane, n-hexane, cyclohexane or heptane may be used. However, the above-mentioned alcohol or its derivative such as the acetal, ketal or alkyl orthoformate may be added in an amount of at least the stoichiometric amount relative to DCPD so that it per se serves as the solvent.

Further, it should be mentioned that water, acetic acid or N,N-dimethylformamide is not desirable as the solvent since such a solvent tends to decrease the yield of TCDE.

The amount of the solvent is not critical, but is preferably from 0.1 to 3 times by weight, based on DCPD.

Further, it is possible to suppress the formation of by-products such as halides by adding a base which is capable of removing the acid resulting from the catalyst or the oxidizing agent during the reaction. As such a base, it is preferred to use a fatty acid salt such as sodium acetate, sodium propionate or sodium butyrate.

With respect to the reaction temperature, the reaction adequately proceeds at room temperature. However, the reaction may be conducted at a temperature higher than 100° C.

The pressure of carbon monoxide is not critical, but is preferably from atmospheric pressure to 50 kg/cm² G. When the pressure is low, the reaction time will be long and the selectivity for TCDE tends to decrease. The carbon monoxide is not required to be highly pure. For instance, oxo gas which is a mixture of carbon monoxide with hydrogen may be used in the same manner as carbon monoxide and it is industrially advantageous.

The reaction time depends upon e.g. the amount of the catalyst or the pressure of carbon monoxide. However, the reaction is usually completed from 15 minutes to 2 hours. Under a condition where the reaction time is prolonged, there is a tendency that the yield of TCDE decreases.

TCDE thus obtained is then subjected to hydrolysis.

The hydrolysis may be conducted either by a method wherein an acid such as hydrochloric acid or sulfuric acid is used or by a method wherein a base such as an aqueous sodium hdyroxide solution or an aqueous potassium hydroxide solution is used. However, it is preferred to use a base, since the reaction thereby proceeds readily and quantitatively, whereby a di-alkali metal salt of tricyclo[5,2,1,0²,⁶]dec-3-ene-8,9-dicarboxylic acid is obtainable.

The hydrolysis by means of such a base may be conducted by a method wherein the starting material TCDE is dissolved in an alcohol solvent such as ethanol or propanol, then an aqueous alkaline solution is added in an amount slightly in excess of the theoretical amount, and the mixture is stirred for 1 to 2 hours at a temperature around the reflux temperature of the alcohol, whereby the reaction can be readily completed. The alkali metal salt thus obtained may be subjected to treatment with an acid such as hydrochloric acid or sulfuric acid, whereby TCDC is obtainable.

This TCDC may be recrystallized from a solvent such as acetonitrile, whereby the purified product is obtainable as white crystals.

Further, when this TCDC is reacted with a dehydrating agent, TCDA is obtainable. As such a dehydrating agent, there may be mentioned acid anhydrides such as acetic anhydride, propionic anhydride or succinic anhydride. The dehydrating agent is usually used in an amount of 2 to 3 times the theoretical molar amount relative to the starting material TCDC, whereby the reaction is facilitated. The reaction temperature is usually from 100° to 150° C., whereby the reaction will be completed in from 1 to 3 hours.

After the reaction, the reaction solution is concentrated, and the residue is dried under reduced pressure, whereby crude TCDA crystals are obtainable. The crude crystals may be recrystallized from a solvent such as cyclohexane, whereby crystals having high purity are obtainable.

Further, it has been surprisingly found that when the diesterification reaction of the present invention is conducted under the above-mentioned reaction conditions except that a tertiary alcohol is used as the alcohol, it is possible to obtain TCDA directly. As such a tertiary alcohol, there may be used t-butyl alcohol, t-amyl alcohol, borneol or linalool. Further, it has been found that when allyl alcohol is used as the alcohol, TCDA is obtainable in a substantial amount although the main product is TCDE. Furthermore, it has been found that when ethylene glycol is used in combination with a fatty acid salt as an additive, TCDA is produced as the main product although TCDE is produced as a by-product. In the case of ethylene glycol, the conversion of DCPD and the selectivity for TCDA are high, and accordingly the yield of TCDA is high.

Now, a process for producing TCDE from TCDC will be described.

In this process, an excess amount of alcohol and a catalytic amount of an acid are added to a predetermined amount of TCDC, and the resulting water is removed under reduced pressure or by azeotropic distillation with benzene or toluene as the solvent.

As such an acid, there may be mentioned a mineral acid such as sulfuric acid or hydrochloric acid, an organic acid such as an aromatic sulfonic acid, and a Lewis acid such as a boron fluoride ether complex.

As the alcohol to be used in this process, there may be mentioned, for instance, an alkyl alcohol, an alkenyl alcohol or a cycloalkyl alcohol.

Now, the present invention will be described in further detail with reference to Examples. However, it should be understood that the present invention is by no means restricted by these specific examples.

EXAMPLE 1: (DIMETHYLESTER)

Into a hastelloy autoclave having an internal capacity of 100 ml, 3.95 g (30 mmol) of DCPD, 0.267 g (1.5 mmol) of palladium chloride, 10.4 g (73 mmol) of anhydrous cupric chloride (purity: 95%) and 24 g of methanol were fed. After feeding carbon monoxide under pressure of 35 kg/cm² G, the reaction was initiated at room temperature (25° C.). The absorption of carbon monoxide started immediately, and 15 minutes later, the pressure became 5 kg/cm² G and the absorption stopped. The reaction was exothermic, and the temperature reached to the maximum of 48° C. The stirring was continued for further 15 minutes, and then the reaction was terminated. After the autoclave was cooled to room temperature, carbon monoxide was removed, and the reaction solution was withdrawn.

The reaction solution was subjected to a concentration operation to remove the solvent. Then, the reaction product was extracted with n-hexane. The n-hexane solution was analyzed by gas chromatography, whereby it was found that no starting material DCPD remained and substantially a single peak was detected for the product.

The above-mentioned reaction was repeated 5 times in exactly the same manner. Each time, the reaction solution was concentrated, and the reaction product was extracted with n-hexane. The 5 n-hexane solutions thus obtained were put together, further concentrated and then subjected to distillation under reduced pressure, whereby 33 g of a fraction of from 140° to 145° C./0.7 mmHg was obtained.

The analytical results of this fraction were as follows.
IR(NaCl): 2930, 1730, 1430 1200 (cm$^{-1}$)
$^{13}$C-NMR(CDCl$_3$): 174.1, 173.9, 131.9, 131.5, 52.5, 51.5, 46.4, 44.3, 43.3, 43.1, 41.8, 38.7, 32.3 (δPPM)
Mass spectrum (m/e (%)): 250 (M$^+$, 25), 218 (100), 124 (63), 66 (80)
Elementary analysis: As $C_{14}H_{18}O_4$

| % | C | H | O |
|---|---|---|---|
| Measured values | 68.38 | 7.51 | — |
| Theoretical values | 67.18 | 7.25 | 25.57 |

From the above results, this fraction was found to be dimethyl tricyclo[5,2,1,0$^{2,6}$]dec-3-ene-8,9-dicarboxylate (hereinafter referred to as "TCDME") represented by the formula:

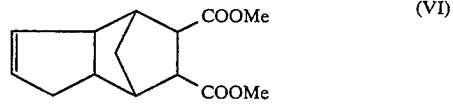 (VI)

From the quantitative analysis of the n-hexane solution by gas chromatography, the yield of TCDME was found to be 98%.

EXAMPLES 2 AND 3: (TCDME)

The reaction was conducted in the same manner as in Example 1 except that a part or whole of the methanol in Example 1 was replaced by methyl orthoformate. The results thereby obtained are shown in Table 1.

TABLE 1

| Example | Alcohol or methyl orthoformate | Yield of TCDME (%) | Conversion of DCPD (%) |
|---|---|---|---|
| 2 | CH$_3$OH 12 g + HC(OCH$_3$)$_3$ 12 g | 96 | 100 |
| 3 | HC(OCH$_3$)$_3$ 24 g | 65 | 94 |

EXAMPLES 4 TO 11: (TCDME)

The reaction was conducted in the same manner as in Example 1 except that the type of the catalyst and the oxidizing agent, the molar ratio of the catalyst to the oxidizing agent and the reaction time were varied as shown in Table 2. The results thereby obtained are shown in Table 2.

TABLE 2

| Examples | Palladium catalyst g (mM) | Oxidizing agent g (mM) | Time hr | Yield of TCDME (%) | Conversion of DCPD (%) |
|---|---|---|---|---|---|
| 4 | Pd(OAc)$_2$ 0.34 (1.5) | CuCl$_2$ 10.4 (73) | 0.7 | 97 | 100 |
| 5 | Pd(NO$_2$)$_2$ 0.34 (1.5) | " | " | 98 | 100 |
| 6 | PdSO$_4$.2H$_2$O 0.36 (1.5) | " | " | 83 | 94 |
| 7 | PdCl$_2$ 0.27 (1.5) | CuCl$_2$.2H$_2$O 12.9 (60) | " | 50 | 70 |
| 8*1 | " | Cu(oAC)$_2$.H$_2$O 12.0 (60) | 1.5 | 16 | 18 |
| 9 | PdCl$_2$ 0.053 (0.3) | CuCl$_2$ 10.4 (73) | " | 58 | 75 |
| 10*2 | " | " | 0.7 | 77 | 100 |
| 11 | None | " | 2 | 21 | 28 |

*1 reaction temperature: 60° C.
*2 reaction temperature: 100° C.

EXAMPLES 12 TO 14: (TCDME)

The reaction was conducted in the same manner as in Example 1 except that a part or whole of the anhydrous cupric chloride in Example 1 was replaced by molecular oxygen (oxygen pressure: 20 kg/cm$^2$ G, initial reaction pressure: 55 kg/cm$^2$ G) and the proportions of the alcohol and the dehydrating agent were varied as shown in Table 3. The results thereby obtained are shown in Table 3.

TABLE 3

| Examples | Oxidizing agent | Alcohol + dehydrating agent | Time hr | Yield of * TCDME (%) |
|---|---|---|---|---|
| 12 | CuCl$_2$ 2.1 g(15 mM) + O$_2$ | CH$_3$OH 24 g | 1.3 | 31 |
| 13 | CuCl$_2$ 2.1 g(15 mM) + O$_2$ | CH$_3$OH 10 g + HC(OCH$_3$)$_3$ 14 g | 1.8 | 71 |
| 14 | O$_2$ | CH$_3$OH 10 g + HC(OCH$_3$)$_3$ 14 g | 2.3 | 23 |

*Conversion of DCPD: 100%

EXAMPLES 15 TO 16: (TCDME)

The reaction was conducted in the same manner as in Example 1 except that the carbon monoxide pressure was varied as shown in Table 4. The results thereby obtained are shown in Table 4.

TABLE 4

| Example | Carbon monoxide pressure | Yield of TCDME (%)* |
|---|---|---|
| 15 | 3–10 kg/cm$^2$ G | 91 |
| 16 | CO + H$_2$ (1:1 mixed gas), 15–30 kg/cm$^2$ G | 97 |

*Conversion of DCPD: 100%

EXAMPLE 17 TO 20: (TCDME)

The reaction was conducted in the same manner as in Example 1 except that the catalyst in Example 1 was replaced by a palladium-supporting catalyst, and the oxidizing agent, the temperature and reaction time were varied as shown in Table 5. The results thereby obtained are shown in Table 5.

TABLE 5

| Examples | Catalyst g (PdmM) | Oxidizing agent g (mM) | Temperature °C. | Time hr | Yield of TCDME (%) | Conversion of DCPD (%) |
|---|---|---|---|---|---|---|
| 17 | 5% Pd-C 1.1 (1.7) | CuCl$_2$ 10.4 (73) | 30 | 1 | 84 | 92 |
| 18 | 5% Pd-C 0.32 (0.5) | CuCl$_2$ 10.4 (73) | 90 | 0.5 | 75 | 100 |
| 19* | 5% Pd-C 1.1 (1.7) | CuCl$_2$ 2.1 (15) O$_2$ | 60 | 1 | 71 | 100 |
| 20 | 5% Pd-Alumina 1.1 (1.7) | CuCl$_2$ 10.4 (73) | 30 | 0.5 | 96 | 100 |

*MeOH 14 g + HC(OCH$_3$)$_3$ 10 g

EXAMPLE 21: (TCDME)

Into a four-necked 2 liter glass flask, 212 g (1.6 mol) of DCPD, 4.0 g (0.023 mol) of palladium chloride, 465 g (3.5 mol) of anhydrous cupric chloride (purity: 95%) and 800 g of methanol were fed. After the temperature was raised to 50° C., carbon monoxide was supplied for 2 hours at a flow rate of 2 liter/min under atmospheric pressure while stirring.

After the reaction, the reaction mixture was cooled, and after removing the solvent, the reaction product was extracted with n-hexane. The hexane solution thereby obtained was concentrated and subjected to distillation under reduced pressure, whereby 284 g of TCDME (purity: 98%) was obtained at from 135° to 143° C./0.5 mmHg.

EXAMPLE 22: (DI-N-BUTYLESTER)

The reaction was conducted in the same manner as in Example 1 except that the methyl alcohol in Example 1 was replaced by n-butanol and the reaction time was changed to 1.8 hours. The reaction solution was subjected to a concentration operation to remove the solvent, and then the reaction product was extracted with n-hexane. The n-hexane solution thereby obtained was analyzed by gas chromatography, whereby it was found that no starting material DCPD remained and the main product was formed at a concentration of 82%.

This main product was purified by column chromatography and then analyzed. The results were as follows.

IR(NaCl): 2900, 1720, 1180 (cm$^{-1}$)

Mass spectrum (m/e (%)): 334 (20), 261 (80), 205 (100), 66 (85).

Elementary analysis: As $C_{19}H_{26}O_4$

| % | C | H | O |
|---|---|---|---|
| Measured values | 70.72 | 8.11 | — |
| Theoretical values | 71.67 | 8.23 | 20.10 |

From the above results, this main product was found to be di-n-butyl tricyclo[5,2,1,0$^{2,6}$]dec-3-ene-8,9-dicarboxylate represented by the formula:

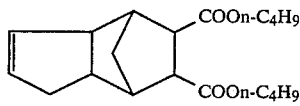

(VII)

EXAMPLE 23: (TCDC)

25 g of TCDME was mixed with 100 g of ethanol and 50 g of a 50% potassium hydroxide aqueous solution, and the mixture was refluxed at 78° C. for 2 hours, whereby crystals were precipitated. The crystals were collected by filtration, then washed with hexane and dried under reduced pressure, whereby 22 g of crude crystals were obtained. These crystals were recrystallized from an acetonitrile solvent, whereby white crystals were obtained. These crystals were dissolved in tetrahydrofuran and analyzed by gas chromatography, whereby they showed a single peak and had a retention time different from the retention time of the starting material TCDME, and the retention time was shortened by trimethylsilylation.

Further, these crystals were subjected to the following analysis.

IR(kBr): 2960, 1700, 1420, 1240, 920 (cm$^{-1}$)

$^{13}$C-NMR(CD$_2$OH): 177.5, 177.2, 132.7, 132.3, 53.5, 47.5, 45.3, 44.4, 44.1, 42.8, 39.1, 32.7 (δPPM)

Mass spectrum (as silylated by bis(trimethylsilyl)acetamide): (m/e (%)): 366 (10), 351 (71), 255 (46), 147 (76), 73 (100).

Elementary analysis: As $C_{12}H_{14}O_4$

| % | C | H | O |
|---|---|---|---|
| Measured values | 65.41 | 7.30 | — |
| Theoretical values | 64.85 | 7.35 | 27.8 |

Melting point: 167.5°–168.0° C.

From the above results, crystals were found to be TCDC.

EXAMPLE 24: (TCDA)

22 g of TCDC and 100 g of acetic anhydride were refluxed at 140° C. for 2 hours. After distilling off the solvent, the reaction mixture was dried under reduced pressure, whereby 20 g of crude crystals were obtained. The crude crystals were recrystallized from a cyclohexane solvent, whereby light yellow crystals were obtained. These crystals were dissolved in chloroform and analyzed by gas chromatography, whereby they showed a single peak at a position whereby the retention time is different from that of the starting material TCDC. Further, these crystals were subjected to the following analysis.

IR (KBr): 2960, 1860, 1790, 1218, 1090, 925 (cm$^{-1}$)

$^{13}$C-NMR(CDCl$_3$): 174.6, 174.2, 132.4, 131.0, 51.7, 45.6, 45.4, 43.9, 42.9, 41.0, 36.5 32.0 (δPPM)

Mass spectrum (m/e (%)): 204 (M$^+$, 15), 176 (45) 131 (35), 66 (100)

Elementary analysis: As $C_{12}H_{12}O_2$

| % | C | H | O |
|---|---|---|---|
| Measured values | 70.91 | 5.78 | — |
| Theoretical values | 70.57 | 5.92 | 23.51 |

Melting point: 93.0°–93.5° C.

From the above results, these crystals were found to be TCDA.

EXAMPLE 25: (DI-N-DECYLESTER)

Two drops of concentrated sulfuric acid was added to a mixture of 3 g of TCDC and 20 g of n-decyl alcohol, and the mixture was reacted under reduced pressure in a bath of 180° C. for 2 hours while removing water. The reaction solution was analyzed by gas chromatography, whereby a peak of a single product was observed while unreacted TCDC was found to be slightly present. After distilling off the excess n-decyl alcohol from the reaction solution, chloroform and an aqueous alkaline solution were added to the residue to neutralize it, followed by water removal and concentration. The concentrated product was purified by column chromatography (by means of Wako gel C-200). The purified product was analyzed. The results were as shown below.

IR(NaCl): 2900, 1720, 1180 (cm$^{-1}$)

Mass spectrum (m/e (%)): 502 (4), 397 (8), 345 (22), 205 (100), 137 (14).

Elementary analysis: As $C_{32}H_{54}O_4$

| % | C | H | O |
|---|---|---|---|
| Measured values | 76.24 | 10.82 | — |
| Theoretical values | 76.49 | 10.76 | 12.75 |

From the above results, this product was found to be didecyl tricyclo[5,2,1,0$^{2,6}$]dec-3-ene-8,9-dicarboxylate represented by the formula:

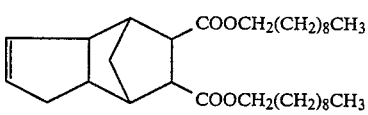

(VIII)

EXAMPLE 26: (DIALLYLESTER)

The reaction was conducted in the same manner as in Example 25 except that the alcohol was changed to allyl alcohol and the temperature of the bath was changed to 160° C. The reaction solution was analyzed by gas chromatography, whereby a peak of a single product was observed while unreacted TCDC was found to be slightly present. The after-treatment and purification were conducted in the same manner as in Example 25. The analytical results were as shown below.

IR(NaCl): 2900, 1720, 1180 (cm$^{-1}$)

Mass spectrum (m/e (%)): 302 (5), 245 (59), 203 (100), 98 (57)

Elementary analysis: As $C_{18}H_{22}O_4$

| % | C | H | O |
|---|---|---|---|
| Measured values | 71.49 | 7.25 | — |
| Theoretical values | 71.52 | 7.28 | 21.19 |

From the above results, this main product was found to be diallyl tricyclo[5,2,1,0$^{2,6}$]dec-3-ene-8,9-dicarboxylate represented by the formula:

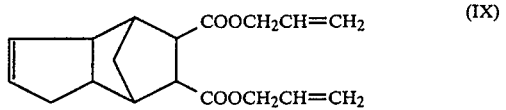
(IX)

EXAMPLE 27: (DICYCLOHEXYL ESTER)

Mass spectrum (m/e (%)): 386 (1), 305 (8), 205 (100), 67 (19).

Elementary analysis: As $C_{24}H_{34}O_4$

| % | C | H | O |
|---|---|---|---|
| Measured values | 74.50 | 8.93 | — |
| Theoretical values | 74.61 | 8.81 | 16.58 |

From the above results, this main product was found to be dicyclohexyl tricyclo[5,2,1,0$^{2,6}$]dec-3-ene-8,9-dicarboxylate represented by the general formula:

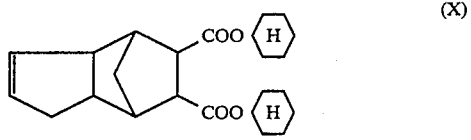
(X)

EXAMPLES 28 TO 33: (TCDE)

The reaction was conducted in the same manner as in Example 1 except that the type of the alcohol, the temperature and the reaction time were changed as shown in Table 6. The results thereby obtained are shown in Table 6.

TABLE 6

| Examples | Alcohol | Temperature (°C.) | Time hr | TCDE obtained (yield (%)) |
|---|---|---|---|---|
| 28 | n-C$_{10}$H$_{21}$OH | 80 | 2 | 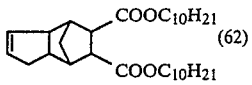 (62) |
| 29 | sec-C$_4$H$_9$OH | 30 | 0.5 | 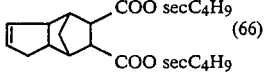 (66) |
| 30 |  | " | 4 | 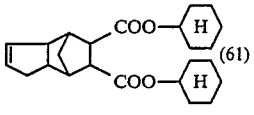 (61) |
| 31 | CH$_2$=CHCH$_2$OH | " | 0.5 | 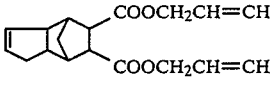 (64)*$^1$ |
| 32 | HOCH$_2$CH$_2$OH | 110 | 0.8 | 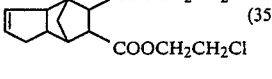 (35) |
| 33*$^2$ | " | 70 | 1 | 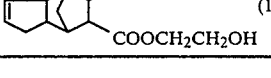 (13) |

*$^1$Yield of TCDA: 28%
*$^2$5.8 g (60 mM) of C$_2$H$_5$COONa was added, the yield of TCDA: 58%

The reaction was conducted in the same manner as in Example 25 except that the alcohol was changed to cyclohexanol. The after-treatment and purification were conducted also in the same manner as in Example 25. The analytical results were as shown below.

IR(NaCl): 2900, 1720, 1180 (cm$^{-1}$)

EXAMPLES 34 TO 38: (TCDA)

The reaction was conducted in the same manner as in Example 1 except that the type of the alcohol, the temperature and the reaction time were changed as shown in Table 7. The results thereby obtained are shown in Table 7.

TABLE 7

| Examples | Alcohol | Temperature °C. | Time hr | Yield of TCDA (%) | Conversion of DCPD (%) | Note |
| --- | --- | --- | --- | --- | --- | --- |
| 34 | tert-butyl alcohol | 30 | 2 | 25 | 33 | |
| 35 | tert-butyl alcohol | 100 | 1 | 52 | 100 | |
| 36 | tert-amyl alcohol | 30 | 3 | 12 | 18 | |
| 37 | allyl alcohol | 30 | 0.5 | 28 | 96 | Yield of TCDE 64% |
| 38* | ethylene glycol | 70 | 1 | 58 | 100 | Yield of TCDE 13% |

*$C_2H_5COONa$ 5.8 g (60 mM)

We claim:

1. A compound represented by the general formula:

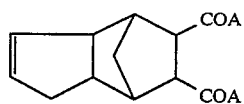

(I)

where each A is —OH or —OR where R is an alkyl group, an alkenyl group or a cycloalkyl group, or both A together represent a >O group.

2. The compound according to claim 1, which is represented by the formula:

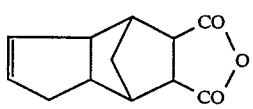

(II)

3. The compound according to claim 1, which is represented by the formula:

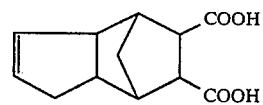

(III)

4. The compound according to claim 1, which is represented by the formula:

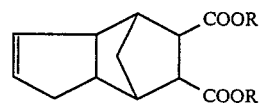

(IV)

where R is a $C_1$–$C_{12}$ alkyl group, a $C_2$–$C_5$ alkenyl group or a $C_5$–$C_6$ cycloalkyl group.

* * * * *